United States Patent
O'Connor

(10) Patent No.: US 10,458,985 B2
(45) Date of Patent: Oct. 29, 2019

(54) CELL-SURFACE MARKER OF EARLY MSC AGING

(71) Applicant: The Administrators of the Tulane Educational Fund, New Orleans, LA (US)

(72) Inventor: Kim C. O'Connor, New Orleans, LA (US)

(73) Assignee: The Administrators of the Tulane Educational Fund, New Orleans, LA (US)

( * ) Notice: Subject to any disclaimer, the term of this patent is extended or adjusted under 35 U.S.C. 154(b) by 181 days.

(21) Appl. No.: 15/302,462

(22) PCT Filed: Apr. 10, 2015

(86) PCT No.: PCT/US2015/025411
§ 371 (c)(1),
(2) Date: Oct. 6, 2016

(87) PCT Pub. No.: WO2015/157694
PCT Pub. Date: Oct. 15, 2015

(65) Prior Publication Data
US 2017/0016898 A1    Jan. 19, 2017

Related U.S. Application Data

(60) Provisional application No. 61/978,708, filed on Apr. 11, 2014.

(51) Int. Cl.
*G01N 33/569* (2006.01)
*C12N 5/0789* (2010.01)
(Continued)

(52) U.S. Cl.
CPC ... *G01N 33/56966* (2013.01); *C07K 14/4747* (2013.01); *C07K 14/70578* (2013.01);
(Continued)

(58) Field of Classification Search
CPC ............ G01N 33/56966; G01N 15/14; G01N 2333/70596; G01N 2333/70578;
(Continued)

(56) References Cited

U.S. PATENT DOCUMENTS

2012/0276064 A1   11/2012  Blau et al.
2014/0065112 A1    3/2014  Madonna et al.
2014/0322811 A1   10/2014  Kang et al.

FOREIGN PATENT DOCUMENTS

WO   WO2004/084921      10/2004
WO   WO 2012/088225   *  6/2012   ............... C12N 1/04
(Continued)

OTHER PUBLICATIONS

Ren et al. Senescence of Cultured Bone Marrow Stromal Cells. Biology of Blood and Marrow Transplantation 17(2): (Feb. 2011) IDS.*
(Continued)

*Primary Examiner* — Gailene Gabel
(74) *Attorney, Agent, or Firm* — Boulware & Valoir

(57) ABSTRACT

This invention relates to a cell-surface marker for identifying MSC that are aging. This invention also relates to a method of screening MSCs of low proliferation potential and trilineage potential by removing CD264+ MSCs from the population.

6 Claims, 9 Drawing Sheets

(51) Int. Cl.
C12N 5/0775 (2010.01)
C07K 14/705 (2006.01)
C07K 14/47 (2006.01)
G01N 15/14 (2006.01)
(52) U.S. Cl.
CPC .......... *C12N 5/0647* (2013.01); *C12N 5/0663* (2013.01); *C12N 5/0665* (2013.01); *G01N 15/14* (2013.01); *G01N 2333/70578* (2013.01); *G01N 2333/70596* (2013.01)
(58) Field of Classification Search
CPC .......... C07K 14/4747; C07K 14/70578; C12N 5/0663; C12N 5/0647; C12N 5/0665
See application file for complete search history.

(56) References Cited

FOREIGN PATENT DOCUMENTS

| WO | WO2012088225 | 6/2012 |
|----|--------------|--------|
| WO | WO2013/067038 | 5/2013 |
| WO | WO2013/121426 | 8/2013 |
| WO | WO2015157694 | 10/2015 |

OTHER PUBLICATIONS

Ren et al. Senescence of Cultured Bone Marrow Stromal Cells. Biology of Blood and Marrow Transplantation 17(2) (Feb. 2011).*
Russell et al., Clonal analysis of proliferation potential of human bone marrow mesenchymal stem cells as a function of potency. Biotechnol Bioeng, 108: 2716-26 (2011).
Yulyana et al., Carbenoxolone Enhances TRAIL-Induced Apoptosis Through the Upregulation of Death Receptor 5 and Inhibition of Gap Junction Intercellular Communication in Human Glioma, Stem Cells and Development vol. 22, No. 13, 2013.
Szegezdi et al., Stem cells are resistant to TRAIL receptor-mediated apoptosis, J. Cell. Mol. Med. vol. 13, No. 11-12, 2009 pp. 4409-4414.
Jin, HJ et a., Comparative Analysis of Human Messenchymal Stem Cells from Bone Marrow, Adipose Tissue, and Umbilical Cord Blood as Sources of Cell Therapy, Int. J. Mol. Sci., 2013, vol. 14, pp. 17986-18001.
Corselli Mirko et al:Cytometry. PA, John Wiley & Sons, Inc, US, val. 83, No. 8, Aug. 1, 2013 (Aug. 1, 2013), pp. 714-720, XP009186140, ISSN: 1552-4930, DOI: 10.1002/CYTO.A.22313.
Bisgin Atil et al:BMC Musculoskeletal Disorders, Biomed Central, London, GB, val. 11, No. 1, Aug. 27, 2010 (Aug. 27, 2010), p. 192, XP021 076255, ISSN: 1471-2474, DOI: 10.1186/1471-2474-11-192.
Nn: GeneT ex Inc, Jan. 1, 2013 (Jan. 1, 2013), XP055407967, Retrieved from the Internet on Sep. 19, 2017: URL:http://www.genetex.com/DcR2-CD264-antibody-TRAIL-R4-01-Functionai-Grade-GTX79874.html.
L. Guida et al: International Journal of Immunopathology and Pharmacology, val. 21, No. 4, Oct. 1, 2008 (Oct. 1, 2008), pp. 921-928, XP055408385, GB ISSN: 0394-6320, DOI: 10.1177/039463200802100416.
Z. Gu et al: Experimental and Clinical Endocrinology and Diabetes., val. 121, No. 10, Nov. 25, 2013 (Nov. 25, 2013), pp. 607-613, XP055408392, DE ISSN: 0947-7349, DOI: 10.1055/s-0033-1354380.
Wagner et al., How to Track Cellular Aging of Mesenchymal Stromal Cells? Aging, Apr. 2010, vol. 2, No. 4, 224-230.
Secchiero et al, Tumor Necrosis Factor-Related Apoptosis-Inducing Ligand Promotes Migration of Human Bone Marrow Multipotent Stromal Cells. Stem Cells 2008; 2955-2964.
Ren et al., Senescence of Cultured Bone Marrow Stromal Cells. Biology of Blood and Marrow Transplantation, Feb. 2011; 17(2).
Degli-Esposti et al., The Novel Receptor TRAIL-R4 Induces NF-κB and Protects against TRAIL-Mediated Apoptosis, yet Retains an Incomplete Death Domain. Immunity (1997), vol. 7, 813-820.
Collado et al., Senescence in premalignant tumours. Nature (2005), vol. 436, p. 642 (Supplementary Information).
Zhu et al., Effects of estrogen on stress-induced premature senescence of vascular smooth muscle cells: A novel mechanism for the "time window theory" of menopausal hormone therapy. Atherosclerosis 215 (2011) 294-300.
Kim et al., Evaluation of premature senescence and senescence biomarkers in carcinoma cells and xenograft mice exposed to single or fractionated irradiation. Oncology Reports 31: 2229-2235, 2014.
Russell et al., Cell-surface expression of neuron-glial antigen 2 (NG2) and melanoma cell adhesion molecule (CD146) in heterogeneous cultures of marrow-derived mesenchymal stem cells. Tissue Eng Part A, 19: 2253-66 (2013).

* cited by examiner

FIGURE 2 Two different MSC sort strategies.

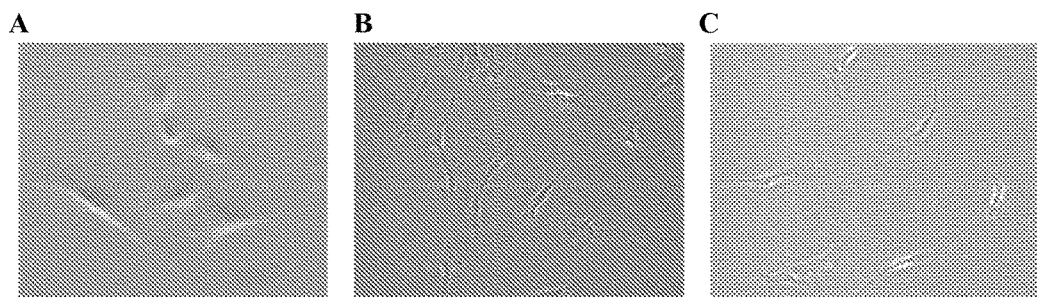
FIGURE 4A-C: Representative images of stained cell culture in the surface marker negative population.
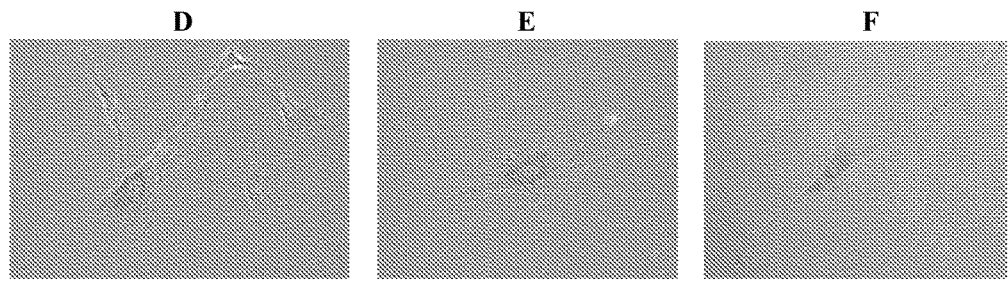
FIGURE 4D-F: Representative images of stained cell culture in the surface marker positive population.

CELL-SURFACE MARKER OF EARLY MSC AGING

PRIOR RELATED APPLICATIONS

This application claims priority to 61/978,708, filed Apr. 11, 2014 and PCT/US15/25411, filed Apr. 10, 2016, each of which is incorporated by reference herein in its entirety for all purposes.

FEDERALLY SPONSORED RESEARCH STATEMENT

This invention was made with government support under Grant No: 1066167 awarded by the National Science Foundation. The government has certain rights in the invention.

FIELD OF THE DISCLOSURE

The disclosure generally relates to a method of identifying aging Mesenchymal Stem Cells (MSCs) and a method of enriching a culture of MSCs with high proliferating potential.

BACKGROUND OF THE DISCLOSURE

In stem cell research, studies have been done to study the regenerative properties of human mesenchymal stem cells (MSCs) from bone marrow for the cells' potential therapeutic applications. MSCs are a promising source of adult stem cells for regenerative medicine, however many senescent cells are found in the heterogeneous ensemble of progenitors and lineage-committed cells that are associated with loss of proliferation potential and differentiation potential. Regenerative properties are highly variable among MSC subsets. Consequently, identification and isolation of progenitor subsets in heterogeneous MSC cultures are essential to the development of highly efficacious stem cell therapies. In other words, the elimination of senescent cells from heterogeneous MSC cultures may improve the treatment outcome of autologous MSC therapies by increasing both cell yield and enhancing the integrity of regenerated tissue.

Every human cell has cellular surface markers and receptors which identify it to other cells in the body. In 1999, Pittenger et al. were the first to identify antigens that could be used to reproducibly identify MSCs with similar properties. MSC population homogenization is achieved by detecting surface antigens using fluorescently labeled antibodies and fluorescence-activated cell sorting (FACS). These advancements, as stated above, may remove the negative effects of senescent cells in MSC populations and increase the efficacy of regenerative medicine by enriching healthy cell population.

To separate the senescent cells from heterogeneous MSCs from bone marrow, bio-markers such as antigens Neuron-Glial Antigen 2 (NG2) and Melanoma Cell Adhesion Molecule (CD146) have been discovered. Flow cytometry is used in the sorting process. Cells with high surface expression of the antigen and cells with low surface expression of the antigen can be differentiated and separated by the flow cytometer. This method selects a proliferative phenotype from heterogeneous MSCs during ex vivo expansion. Russell et al., Cell-Surface Expression of Neuron-Glial Antigen 2 (NG2) and Melanoma Cell Adhesion Molecule (CD 146) in Heterogeneous Cultures of Marrow-Derived Mesenchymal Stem Cells. Tissue Engineering: Part A, Vol. 19, No. 19-20, 2013.

Another way to characterize cellular senescence is by using a proliferation dye. This dye can be used to measure the doubling time for MSCs of different sizes and granulation. A parent population is first dyed and then allowed to grow. As the cells divide, the dye is distributed approximately evenly amongst the daughter cells. Cells with a lower doubling time will therefore contain less dye after a given amount of time than cells with a high doubling time. This is because cells that divide rapidly will have distributed the dye amongst more daughters. If a fluorescent proliferation dye is chosen, FACS can be employed to separate subpopulations that either divide rapidly or slowly. A schematic representation of how proliferation dye works to identify rapidly and slowly dividing cells is presented in FIG. 1.

Russell et al. found that NG2 expression is uniquely correlated to rapidly dividing stem cells. Sorting using this surface receptor will enrich the sorted population by concentrating the number of rapidly dividing MSCs. Alternatively, sorting by using the death receptor can result in an enriched parent population using a totally different marker. If the death receptor indicates slowly dividing or senescent cells, then removing these cells from the population will enable the parent population to be more robust. As mentioned above, a boosted population is extremely desirable for stem cell therapies.

A current barrier to realizing the therapeutic potential of MSCs is the inability to identify different MSC populations in a heterogeneous culture. The heterogeneous cultures which include cells with lower proliferation and multipotent potential results in substantial variation and decreases the effectiveness of stem cell therapies with MSCs. Previously, this obstacle was addressed by previously unknown identification of two biomarkers, NG2 and CD146, which select for highly proliferative multipotent MSCs. However, identifying and isolation of early aging MSCs is even more desirable to obtain MSCs with higher regenerative potential and better therapeutic efficacy.

In 2010, Wagner et al states that "No date no specific molecular marker is available that prospectively reflects the degree of cellular aging in MSC." Wagner et al., How to Track Cellular Aging of Mesenchymal Stromal Cells? Aging, April 2010, Vol. 2, No. 4, 224-230.

Secchiero et al. in 2008 found that MSCs express CD264, but did not identify any specific function or properties thereof. Secchiero et al, Tumor Necrosis Factor-Related Apoptosis-Inducing Ligand Promotes Migration of Human Bone Marrow Multipotent Stromal Cells. Stem Cells 2008; 2955-2964 ("the expression of surface TRAIL-R2 and TRAIL-R4 was a general feature of MSCs," where TRAIL-R4 is an acronym of CD264).

Ren et al. in 2011 found that CD264 is expressed at late passage (passage 5-11) MSCs, but not expressed in passage 3. Ren et al., SENESCENCE OF CULTURED BONE MARROW STROMAL CELLS. Biology of Blood and Marrow Transplantation, Feb. 2011; 17(2) ("Flow cytometry analysis confirmed greater expression of TNFRS 1 OD on late passage cells," where TNFRS 10 D is an acronym of CD264).

Further, it has been suggested that CD264 is widely expressed in tissues and therefore is not senescence-related. Degli-Esposti et al., The Novel Receptor TRAIL-R4 Induces NF-KB and Protects against TRAIL-Mediated Apoptosis, yet Retains an Incomplete Death Domain, IMMUNITY (1997), Vol. 7, 813-820. It was also suggested that CD264 is upregulated by oncogene-induced senescence, but "none was found upregulated in association to replicative senescence." Collado et al., Senescence in premalignant tumours, Nature (2005), Vol. 436, p. 642 (Supplementary Information).

Zhu et al. further suggested that CD264 is upregulated by stress-induced premature senescence. Zhu et al., Effects of estrogen on stress-induced premature senescence of vascular smooth muscle cells: A novel mechanism for the "time window theory" of menopausal hormone therapy, Atherosclerosis 215 (2011) 294-300.

Lastly, Kim et al. reported that CD264 expression may "depend upon the specific cellular context and may not be a general marker for cellular senescence." Kim et al., Evaluation of premature senescence and senescence biomarkers in carcinoma cells and xenograft mice exposed to single or fractionated irradiation. Oncology Reports 31: 2229-2235, 2014. This reference teaches away from using CD264 as a marker for early aging MSCs.

SUMMARY OF THE DISCLOSURE

This invention provides a method of use of a cell-surface marker CD264 previously unknown for identifying and sorting early aging MSCs. The marker was previously not related to MSC differentiation and/or proliferation.

The MSCs that positively express CD264 have morphologies consistent with known morphologies of aging MSCs. The resultant culture of isolated cells without expressing CD264 is enriched with MSCs of higher proliferation and differentiation potential with a broad range of regenerative properties of these stem cells, and therefore better efficacy in stem cell treatment schemes.

This disclosure is for a method of characterization of MSC populations sorted by a unique cell death receptor, which is a marker of MSC early aging an/or senescence. Populations of cells with the death receptor can be evaluated for lack of regenerative/differentiation extent and colony-forming efficiency. Healthier population will have a low concentration of the death receptor on its surface, and will also display higher regenerative potential, higher differentiation trilineage potential and high colony-forming efficiency. On the other hand, early aging or senescent cells with a higher concentration of the death receptor underperform their healthy counterparts in both of these categories.

Further, by identifying the early aging or senescent MSCs in a heterogeneous culture, one can enrich the culture with young, non-senescent MSCs by removing the identified MSCs. Or alternatively, the culture having aging MSCs may be rejuvenated when the aging MSCs constitute 50% of the entire population.

Identification of early-aging MSCs is beneficial in determining rejuvenation regime. If, for example, a population of MSCs have more than 50% cells expressing CD264, rejuvenation may be necessary to maintain the proliferation potential of such cells. Rejuvenation is the process of restoring the regenerative properties of MSCs without reprogramming through a pluripotent state. Stem cell rejuvenation is an area of research with the goal of restoring aging stem cells to a younger, more regenerative state without change to their potency. In contrast, reprogramming somatic cells to induced pluripotent stem (iPS) cells resets both their age and potency. Rejuvenation uncouples the resetting of the aging clock from resetting potency. The advantages of rejuvenating MSCs over reprogramming are threefold: (1) avoidance of genetic and epigenetic abnormalities from reprogramming; (2) prevention of teratoma formation from cells in a pluripotent state; and (3) efficiency of rejuvenating MSCs in terms of time, cell yield and cost. With these advantages, rejuvenation is a safer and more efficient alternative to restore the regenerative properties of MSCs than reprogramming.

Currently rejuvenation may be conducted in one of several ways: blocking certain signaling pathways that are related to cell aging, such as p38 MAPK signaling pathway; restoring telomerase activity; providing medium having composition similar to that in young stem cell cultures, among others. When a MSC population having more than 50% of CD264$^+$ cells is identified, proper rejuvenation regime may be able to restore its regenerative and/or proliferative potential.

The CD264 was identified as a novel and unique cell-surface marker of pre-senescent MSCs at an early stage of aging. CD264 is a decoy receptor for tumor necrosis factor-related apoptosis-inducing ligand (TRAIL). CD264 expression inhibits TRAIL-induced cell death and has never been associated with pre-senescent MSCs and has never been used to isolate aging MSCs. Other acronyms of CD264 includes TRAIL-receptor 4 (TRAIL-R4), decoy receptor 2 (DcR2), TRAIL receptor with a truncated death domain (TRUNDD), tumor necrosis factor receptor superfamily member 10d (TNFRSF10D). However, CD264 expression in MSCs is inversely correlated to the rate of cell division; only slowly dividing MSCs express CD264. CD264+ MSCs at early passage (passage 3) have greatly diminished colony-forming efficiency and differentiation potential relative to CD264− MSCs. The morphology of CD264+ MSCs is consistent with an aging cell: large size and granular cytoplasm. While CD264+ MSCs at early passage express beta-galactosidase, they undergo cell division, albeit slowly, and thus are not yet senescent.

The CD264 as a marker has a pattern of expression for certain MSCs after serial passages. A percentage of CD264+ MSCs in a heterogeneous population increases with passage as the overall culture ages. The expression of CD264 was compared with known intracellular proteins that regulate the cell cycle: p16, p21 and p53, and was found to correlate with p21.

CD264 is the only surface marker discovered for early MSC aging and can be used on a method for sorting heterogeneous MCS populations. There are numerous uses of this method in addition to sorting MSCs. CD264 can be used to identify biological agents and culture conditions that could slow the rate of MSC aging and potentially reverse the aging process. In the clinic, the content of CD264+ cells in an MSC therapy could potentially predict its efficacy for a variety of therapeutic applications. Additionally, CD264 could be used to remove aging cells during the production of MSC therapies.

In one aspect, this disclosure provides a method of identifying multipotent mesenchymal stem cells of high proliferation potential or trilineage potential, comprising the steps of a) collecting mesenchymal stem cells, b) measuring the expression of CD264, and c) removing the mesenchymal stem cells with positive expression of CD264.

In another aspect, this disclosure provides a method of identifying multipotent mesenchymal stem cells of high proliferation potential, comprising the steps of: a) collecting mesenchymal stem cells, b) introducing fluorescent antibodies against CD264 to the collected mesenchymal stem cells, c) sorting the mesenchymal stem cells based on fluorescent characteristics thereof, and d) collecting the mesenchymal stem cells that are not bound by the fluorescent antibodies.

In another aspect, this disclosure provides a composition comprising a population of mesenchymal stem cells having a colony forming efficiency of greater than 35% and trilineage potential, at least 50% of said mesenchymal stem cells having negative expression of CD264.

In another aspect, this disclosure provides a cell-surface marker for identifying aging mesenchymal stem cells, wherein the cell-surface marker is CD264.

In another aspect, this disclosure provides a cell-surface mark for identifying mesenchymal stem cells having low proliferation and trilineage potential, wherein the cell-surface marker is CD264.

In one embodiment, CD264 is used as a cell-surface marker for identifying aging MSCs, where the doubling time of $CD264^+$ MSCs is at least twice as long as $CD264^-$ MSCs.

In one embodiment, CD264 is used as a cell-surface marker for identifying aging MSCs, where the colony-forming efficiency of $CD264^+$ MSCs is at least 3-fold less than $CD264^-$ MSCs.

In one embodiment, CD264 is used as a cell-surface marker for identifying MSCs having low proliferation and trilineage potential, wherein the $CD264^-$ MSCs produces at least 3-fold more mineralization than $CD264^+$ MSCs.

In one embodiment, CD264 is used as a cell-surface marker for identifying MSCs having low proliferation and trilineage potential, wherein the $CD264^-$ MSCs produces at least 3-fold more lipids than $CD264^+$ MSCs.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention.

The following abbreviations are used herein:

| ABBREVIATION | TERM |
| --- | --- |
| MSC | Mesenchymal Stem Cell |
| FACS | fluorescence activated cell sorting |
| TRAIL | tumor necrosis factor-related apoptosis-inducing ligand |
| CFU | Colony forming efficiency |
| TRAIL-R4 | Acronym for CD264 |
| DcR2 | Acronym for CD264 |
| TRUNDD | TRAIL receptor with a truncated death domain, acronym for CD264 |
| TNFRSF10D | Tumor necrosis factor receptor superfamily member 10d, acronym for CD264 |

BRIEF DESCRIPTION OF THE DRAWINGS

FIG. 4A-C show representative images of stained cell culture of CD264-negative population, and FIG. 4D-F show representative images of stained cell culture in the surface marker positive population.

FIG. 8A: representative histograms of parental MSCs labeled with isotype at passage 3; FIG. 8B: representative histograms of parental MSCs labeled with anti-CD264-PE at passage 3; FIG. 8C: representative histograms of parental MSCs labeled with isotype at passage 7; FIG. 8D: representative histograms of parental MSCs labeled with anti-CD264-PE at passage 7; FIG. 8E: representative micrographs of colorimetric staining of senescence-associated beta-galactosidase activity of $CD264^-$ MSCs at passage 3; FIG. 8F: representative micrographs of colorimetric staining of senescence-associated beta-galactosidase activity of $CD264^+$ MSCs at passage 3; FIG. 8G: representative micrographs of colorimetric staining of senescence-associated beta-galactosidase activity of CD264− MSCs at passage 7; FIG. 8H: representative micrographs of colorimetric staining of senescence-associated beta-galactosidase activity of CD264+ MSCs at passage 7; FIG. 8I-J: Flow cytometric analysis of scatter properties; FIG. 8K: senescence-associated beta-galactosidase activity for CD264+ and CD264− groups in parental MSCs at passage 3 and 7.

DETAILED DESCRIPTION

Figure 1:
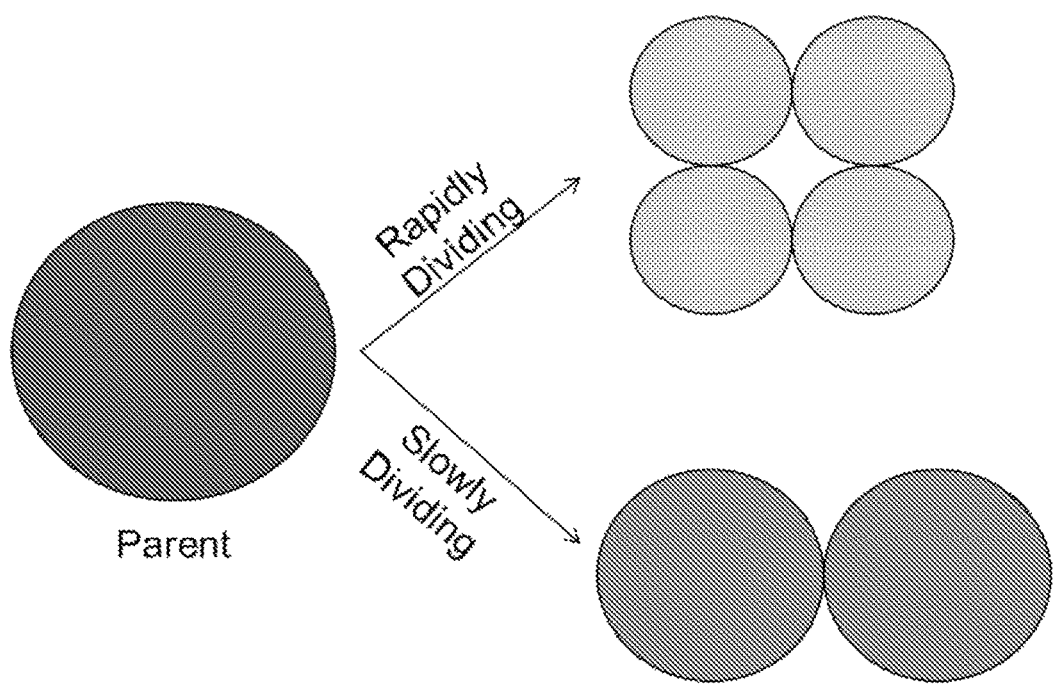
FIG. 1 is a schematic view illustrating how proliferation dye works to distinguish rapidly dividing MSCs from slowly dividing MSCs.

We have identified CD264 as a cell-surface marker of human bone marrow MSCs at an early stage of aging in a pre-senescent state. CD264 is one of four cell-surface receptors (CD261-264) for tumor necrosis factor-related apoptosis-inducing ligand (TRAIL). CD264 is a decoy receptor whose expression inhibits TRAIL-induced cell death. However, CD264 expression has been uniquely correlated to proliferation potential of MSCs among CD261-264. CD264+ MSCs at early passage have limited proliferation and differentiation potential relative to CD264− MSCs, showing that CD264 expression is indicative of an early stage of aging in a pre-senescent state. CD264+ MSCs at early passage have an enlarged, granular morphology and elevated expression of beta-galactosidase as compared with CD264− MSCs. The content of CD264+ cells in MSC cultures increase with serial passage. Further experiments are being conducted to determine the impact of the increasing CD264+ MSC content.

The majority of research on MSCs is on the overall culture, not the underlying heterogeneity. Consequently, cell subsets in heterogeneous MSC cultures are poorly defined. As discussed below, there are numerous basic research and clinical applications of this aging marker.

Inventor's experiments show that CD264, among TRAIL receptors CD261-264, is the only surface marker correlated with MSC early aging. More than 90% of the MSCs in this slowly dividing subset are CD264+ cells. In fact, relative to CD261-CD263, CD264-positive cells were consistently the most prevalent among slowly dividing MSCs (data not shown). CD264 was selected for further analysis because of this strong inverse correlation between surface expression and the rate of cell division in early passage MSCs (data not shown).

MSCs are known to be resistant to TRAIL-induced cell death (Szegezdi et al., 2009). Both CD264− and CD264+ MSCs are equally refractory to this ligand (data not shown). As such, expression of this decoy receptor is not a prerequisite for TRAIL resistance in MSCs.

Further experiments were conducted to verify the trilineage potential of CD264+ and CD264− MSCs, lending support to the use of CD264 expression as the indicator of therapeutic efficacy.

The CD264 expression was also correlated with p21 expression, which is upregulated at an early stage of cell aging. In contrast, the CD264+ MSCs at early passage will be negative for p16 expression, which is upregulated in senescence. The inventor's experiments revealed a clear linkage between CD264 and p21 that may be used to further improve the identification and enrichment procedure.

The conditioned medium from osteogenic culture of CD264+ MSCs will inhibit the osteogenic potential of young CD264− MSCs. Conditioned medium from CD264− MSC culture will reverse MSC aging in part by promoting the osteogenic potential of CD264+ MSCs. Accordingly, conditioned medium from CD26430 MSC culture may improve the efficacy of MSC therapies for bone regeneration (e.g., repair of broken bones, spinal fusion, and the treatment of osteoporosis, to name a few examples). In other words, CD264− conditioned medium can be used to remove inhibitory cells during the production of MSC bone therapies, or prolong the efficacy thereof.

EXAMPLE 1

CD264 as Msc Aging Indicator

Figure 2:
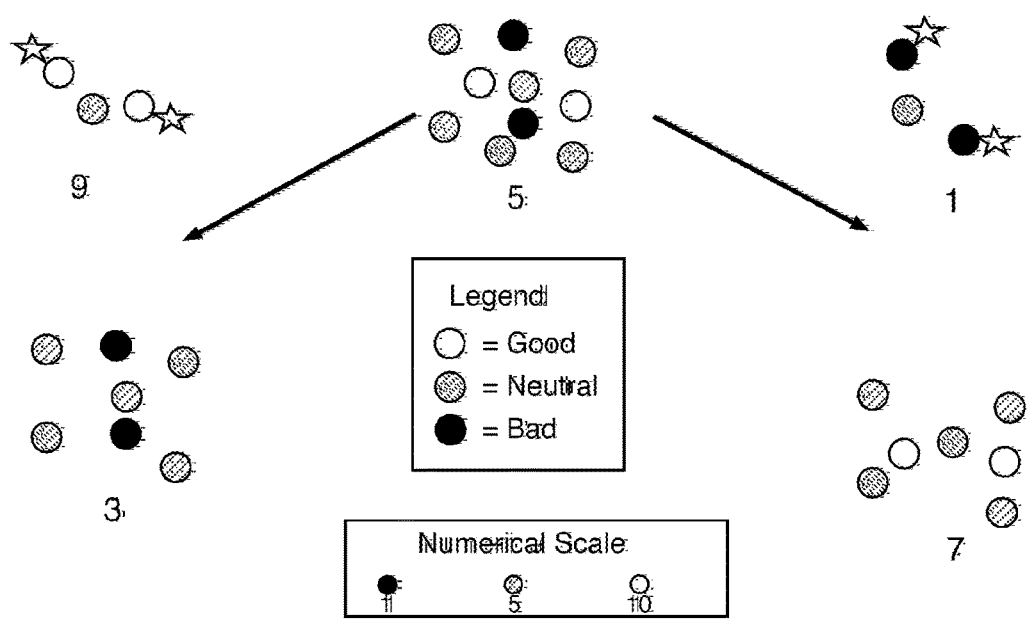
FIG. 2 is a schematic view illustrating different strategies for sorting MSCs.

Heterogeneous MSCs from a single donor's bone marrow are sorted by flow cytometry based on the level of the expression of this surface receptor. The MSCs are separated into two populations: the population that has low expression of the surface marker CD264 and the population that has high expression of the surface marker. The sorting strategy is shown in FIG. 2. Each ball represents a cell. Hollow cells are rapidly dividing, and are therefore the most desired for stem cell therapies. Solid cells are close to senescent and are undesirable. Hatched cells are somewhere in the middle. The number each population is a relative indicator of fitness for use in therapies, with a 10 being the best possible combination. Stars indicate an antibody tag. Left: rapidly dividing MSCs are tagged and sorted using the NG2 cell surface receptor resulting in an enriched sorted population (top). Right: slowly dividing MSCs or those possible close to senescence are sorted for the presence of death receptor. This sort results in an attenuated sorted population (top) but an enhanced parent population (bottom).

The characterization of MSC populations is based on their potency and proliferation. Three assays are used to characterize the two populations of MSCs separated by the surface receptor marker—Colony Forming Unit assay, beta-galactosidase staining, and trilineage potential assay.

Colony forming unit assays study the efficiency with which MSCs form colonies and have proliferative potential. The results of the two populations are compared and used to determine whether a potential relationship between proliferative potential and the surface receptor expression can be demonstrated.

Beta-galactosidase staining is a method to detect beta-galactosidase—enzyme that is associated with senescence. This assay is used to differentiate the senescent cells and all the other cells in the two populations. The results of this assay are used to investigate the percentage of senescent cells in each population.

Trilineage potential assay quantifies the potency of single cell derived MSC colonies. Three different differentiation media are added to the colonies, and the assay quantifies trilineage potential to exhibit osteogenesis, adipogenesis, and chondrogenesis as a measure of potency. The results can be used to compare the potency of the two populations.

Senescence-associated beta-galactosidase activity at pH 6.0 can be detected histochemically in subconfluent cultures, 4 days after inoculation, with the Senescence Beta-Galactosidase Staining kit (Cell Signaling Technology, Danvers, Mass.). Cell images of cultures stained for beta-galactosidase activity were captured with an Optronics DEI-750 digital camera (Goleta, CA) mounted onto an Olympus IX50 microscope (Center Valley, PA). To determine percentage of cells positive for beta-galactosidase activity, images of stained cells are analyzed with the background correction and optical density functions from Image-Pro Plus software (version 6.1, Media Cybernetics, Silver Spring, Md.). Results are reported as a mean value from 30 randomly selected images per sample.

To assess the relationship between proliferation potential and the expression of TRAIL receptors, MSCs were pre-labeled with CellTrace Violet proliferation dye and expanded prior to labeling with antibodies against the TRAIL receptors. The TRAIL receptor expression was examined as a function of the rate of cell division inasmuch as slower growth is a hallmark of cellular aging. Early-passage MSCs were selected for this initial experiment because inventors have demonstrated that these cultures contain cells with a broad spectrum of proliferation potential from rapid to slow cell division. MSCs were labeled with the CellTrace Violet proliferation dye and amplified for 4 days to detect cell division by dye dilution, as described in (Russell et al., 2013). The fluorescence intensity for the CellTrace dye is inversely correlated to the rate of cell division, as shown in FIG. 3.

Figure 3:
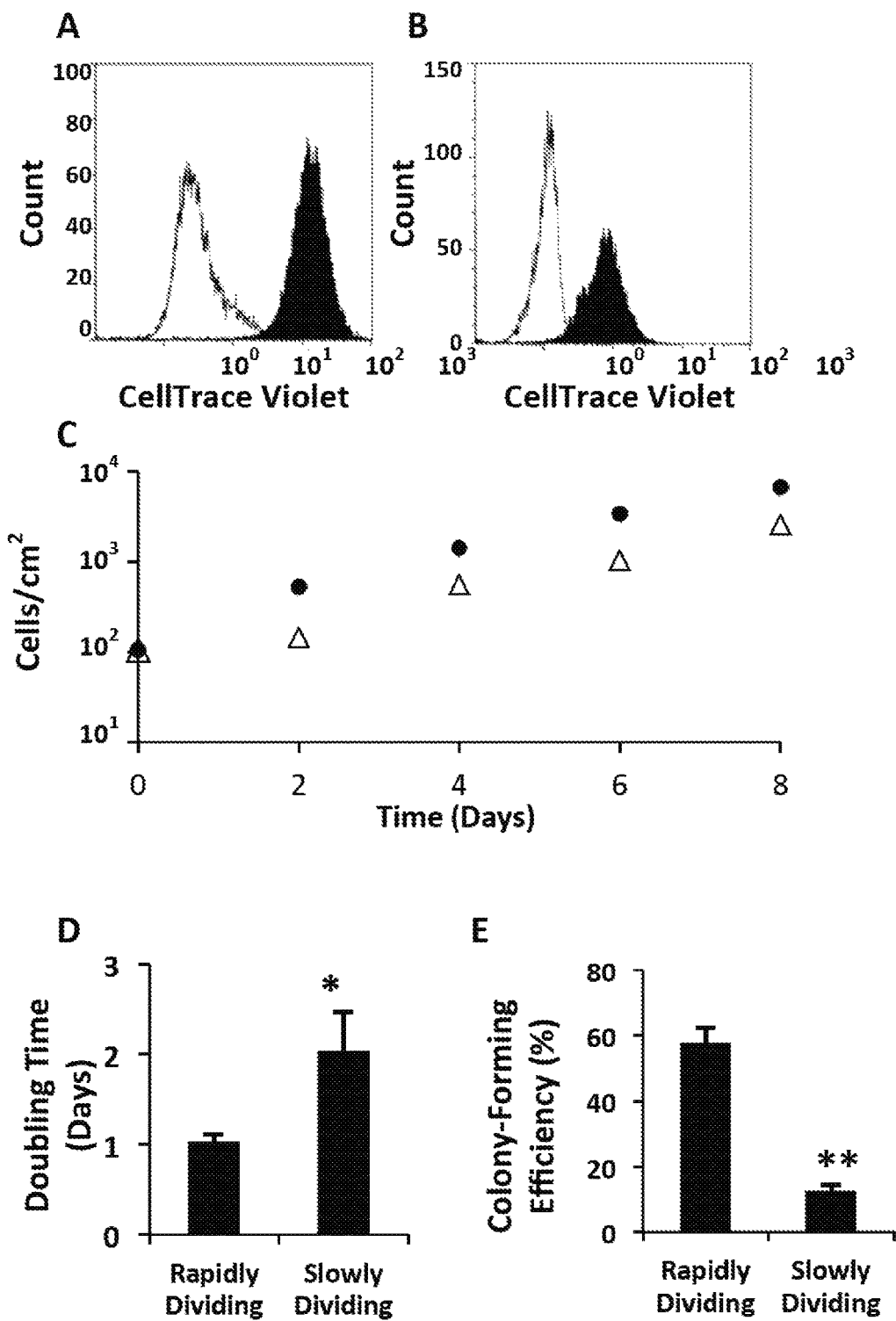
FIG. 3A-E. Proliferation potential of MSCs sorted based on CellTrace Violet fluorescence. Parental MSCs (P2) were labeled with CellTrace Violet and amplified for 4 days. Viable cells with the highest and lowest 10% of fluorescence intensity were sorted by FACS into slowly and rapidly dividing groups, respectively. Representative histograms from FACS analysis of 10,000 cells show (A) parental MSCs labeled with CellTrace Violet at 0 days (black) and 4 days (white), and (B) purity of sorted groups of rapidly (white) and slowly (black) dividing MSCs. (C) Growth curve of rapidly (circles) and slowly (triangles) dividing MSCs and parental MSCs (squares). Doubling times (D) and colony-forming efficiency (E) of sorted groups relative to parental MSCs (n =3). Data are expressed as a mean ±standard error to the mean. *, $p<0.05$ and **, $p<0.01$ vs. rapidly dividing MSCs.

As shown in FIG. 3, the fluorescence intensity of the CellTrace dye is inversely correlated to the rate of cell division. Viable cells with the highest and lowest 10% of fluorescence intensity for CellTrace Violet were FACS sorted into slowly and rapidly dividing cell groups, respectively (FIGS. 3A and B). At early passage, slowly dividing MSCs from the high CellTrace fluorescence group have doubling times that are 80% higher on average than rapidly dividing MSCs from the low CellTrace fluorescence group (FIGS. 3C and D). Besides doubling time, another measure of proliferation potential is the efficiency by which MSCs form colonies when plated at clonogenic levels. The colony-forming efficiency of slowing dividing MSCs from the high CellTrace fluorescence group is 20% on average the value of rapidly dividing MSCs from the low CellTrace fluorescence group (FIG. 3E), consistent with the relative doubling times for these two cell groups.

TABLE 1

P5 7042R beta-galactosidase staining results

| | | Number of b-gal positive cells | Total number of cells | % b-gal positive cells |
|---|---|---|---|---|
| PLATE 1 | surface marker+ | 23 | 98 | 23.5% |
| | surface marker− | 1 | 153 | 0.7% |
| PLATE 2 | surface marker+ | 19 | 109 | 17.4% |
| | surface marker− | 2 | 145 | 1.4% |
| PLATE 3 | surface marker+ | 26 | 100 | 26.0% |
| | surface marker− | 1 | 162 | 0.6% |

TABLE 2

P5 7042 R beta-galactosidase staining result statistical analysis.

| | Average % b-gal positive cells | Standard Deviation |
|---|---|---|
| surface marker positive | 22.3% | 0.0440 |
| surface marker negative | 0.9% | 0.0042 |

The results in Table 2 show that 22.3% cells in the surface marker positive population of P5 7042R MSC cell culture show beta-galactosidase activity, whereas only 0.9% of the cells in the surface marker negative population show beta-galactosidase activity. Since beta-galactosidase is a senescence associated enzyme, it shows that a much greater amount of senescent cells are present in the sorted population that expresses a high level of the surface marker, and a minimal amount of senescent cells are found in the MSC population that expresses a low level of the surface marker.

FIGS. 4A-C show some representative images of stained cell culture, obtained from 7042R MSCs, in the surface marker negative population, while FIGS. 4D-F show some representative images of stained cell culture in the surface marker positive population.

Inventor's experiment also shows that cells negative for CD264 form many more colonies than cells positive for death receptor (data not shown). From simple inspection, it can easily be noticed that the colony forming potential of the receptor-positive cells is much less than the efficiency on its receptor-negative counterparts.

EXAMPLE 2

Proliferative, Osteogenic and Adipogenic Potential for $CD264^+$ and $CD264^-$ MSCS Primary MCSs were harvested from a 2 mL from the iliac crest of healthy adult volunteers. Cell culture reagents were obtained from Invitrogen (Carlsbad, Calif.) unless otherwise noted herein. MSCs were inoculated at $100\pm10$ cells/cm$^2$ into 150 cm$^2$ T-flasks in Complete Culture Media with Antibiotics (CCMA) consisting of 500 mL αMEM with L-gluatmine, 100 mL Fetal Bovine Serum (FBS; HyClone, Logan, UT; final concentration 16.5%), 6 mL L-glutamine (final concentration 2 mM), and 6 mL penicillin/streptomycin (final concentration 100 units penicillin and 100 μg/mL streptomycin). MCSs were maintained at subconfluent in an incubator at 37° C. and 5% $CO_2$. All experiments described were conducted on cells at passages 3-5 unless otherwise noted.

Cell samples for immunolabeling were collected at subconfluent population densities. Cell suspensions of $2\times10^6$ cells/mL Phosphate-Buffered Saline (PBS) were immunolabled in aliquots of 100-500 μL for 30 minutes on ice in the dark with a fluorochrome-conjugated, anti-human monoclonal antibody against the death receptor. Labeled cells were washed three times with PBS and suspended at $5-6\times10^6$ cells/mL.

PBS for flow cytometry or $1-2\times10^6$ cells/mL PBS for cell sorting. Cells were kept on ice up until sorting as described in Russell et at (2013).

Figure 6:
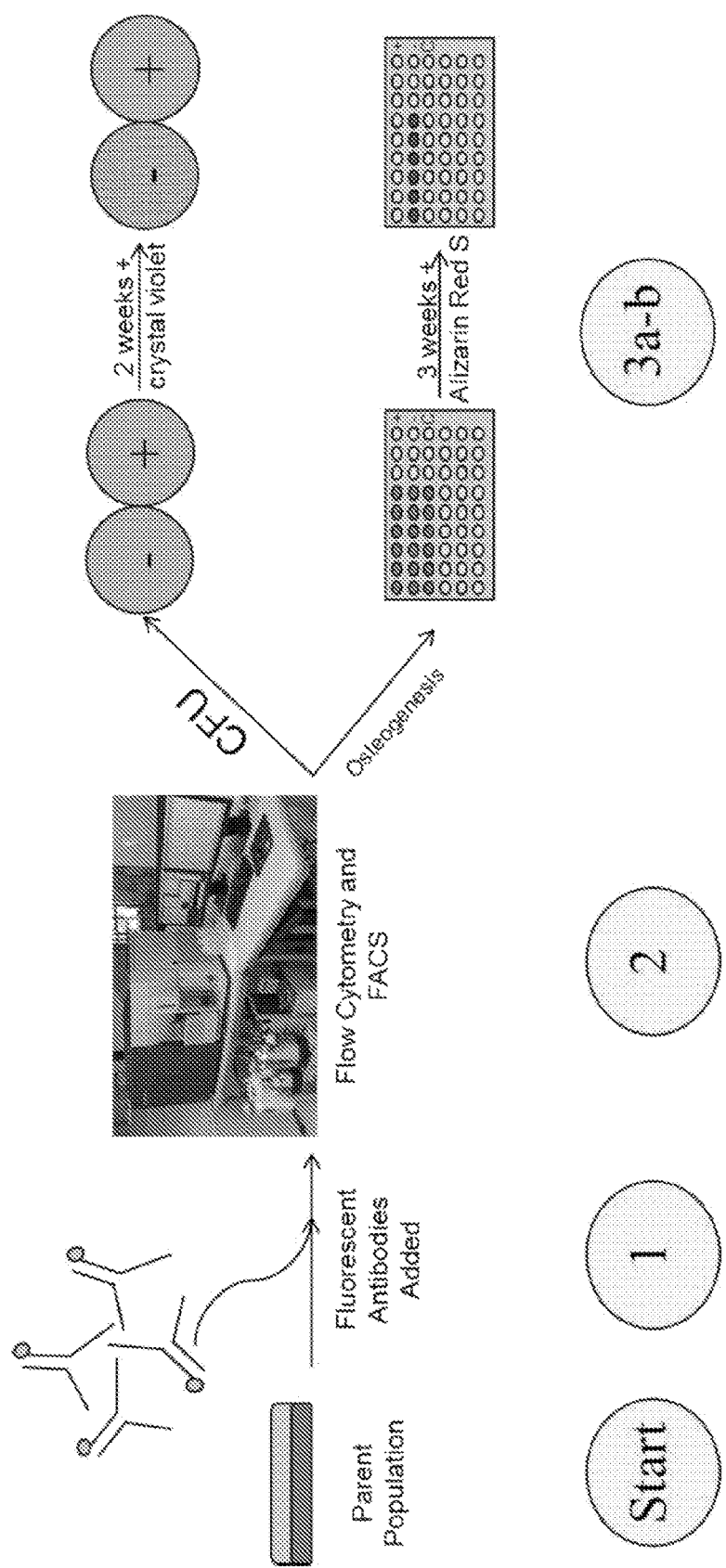
FIG. 6 is schematic views of the methodology employed to determine CFUs and osteogenic potential and quantification.

FIG. 6 shows the methodology for determination of CFUs and osteogenic potential and quantification. (1) The parent population is stained with a fluorescent primary antibody or alternatively with an unlabeled primary antibody followed by a secondary, anti-primary fluorescent antibody. (2) The populations are sorted by FACS. (3a) Cells positive for death receptor are cultured separately from the sorted population (negative). After two weeks, crystal violet staining is performed and the presence of CFUs is quantified by hand. (3b) Death receptor positive and death receptor negative cells are cultured in osteogenic differentiation media for three weeks concurrently with a death receptor negative group cultured in CCMA. After three weeks, all three groups are stained with Alizarin Red S, and a fluorescent plate reader is used to detect the presence of osteoblasts. (FACS image from http:// www.stemcellsaustralia.edu.au/site/DefaultSite/filesystem/images/FACS%20Aria%20III%20at%20MBC%20photo.jpg)

MSCs were inoculated at 100±10 cells in a 10 cm cell culture plates and cultivated at 37° C. and 5% $CO_2$ in CCMA for 14 days. Both MSCs positive and negative for death receptor were cultured. At the conclusion of this period, colonies were washed with water and stained with 3% crystal violet (Sigma-Aldrich, St. Louis, Mo.) in methanol for 20 minutes. Colonies were then washed in tap water until the background was clear. Colonies were counted by visual inspection. Individual, isolated cells were not considered to be colonies.

Differentiation into osteoblasts was induced by bone differentiation media, consisting of 180 mL of low-glucose Dulbecco's Modified Eagle Medium (DMEM), 20 mL FBS, 2 mL penicillin/streptomycin (final concentration 100 units penicillin and 100 μg/mL streptomycin), 100 nM Dexamethasone (Sigma-Aldrich), 10 mM β-glycerolphosphate (Sigma-Aldrich), and 50 μM L-Ascorbic acid 2-phosphate (Sigma-Aldrich). Both death receptor positive and death receptor negative cells were exposed to bone differentiation media. Cells were cultured in a 6-well plate with fresh bone differentiation media added every 2-3 days for 21 days.

Alizarin Red S (Sigma-Aldrich) is used to detect calcium in the sample via a chelation process. The media was aspirated and each well was rinsed with PBS. 200 μL of 4% paraformaldehyde (Sigma-Aldrich) was added to each dish and incubated at room temperature for 20 minutes. The paraformaldehyde was removed and 200 μL of Alizarin Red S was added to each well with an incubation time of 20 minutes at room temperature. The well was washed with water until the background was clear, and a final rinse was conducted using PBS. Quantification is done using a spectrometer and normalizing to control wells which contained only CCMA. FIG. 6 represents the overall methods for Determination of Colony Forming Efficiency (CFU) and Osteogenic Potential and Quantification.

The DNA content of a sample was measured using the Quanti-iT PicoGreen dsDNA Reagent (Invitrogen) following the kit's protocol.

Statistical analysis was completed using a two-tailed, non-paired, equal variance Student's t-Test, as well as one-way, two-way and repeated measures ANOVA with multiple comparison testing.

Figure 5:
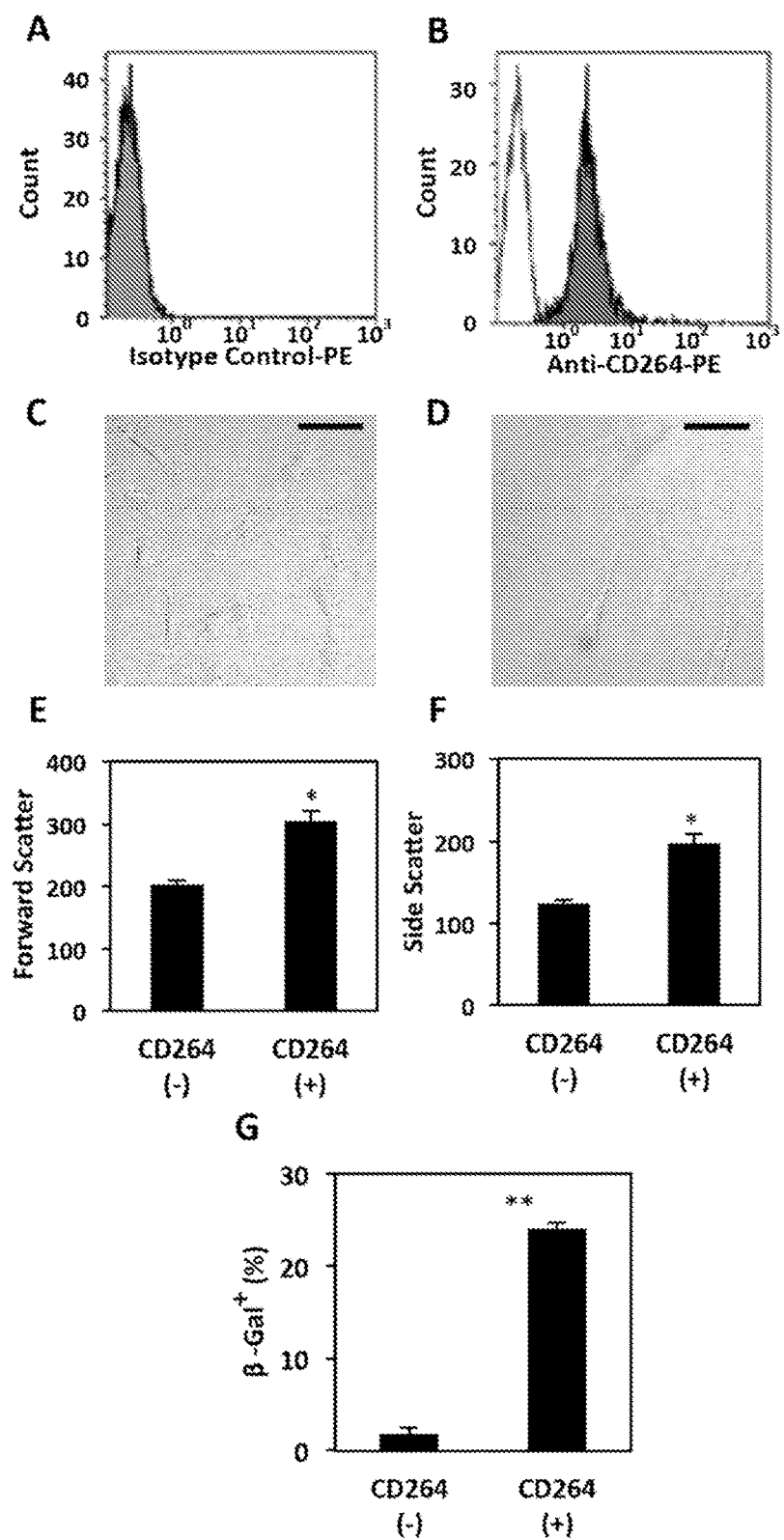
FIG. 5. Morphology and senescence of $CD264^-$ and $CD264^+$ MSCs. P3 MSCs were labeled with anti-CD264-PE and FACS sorted into CD264-negative and -positive populations based on the isotype control. Histograms depict purity of the sort groups, which was evaluated by reanalysis of (A) the isotype and (B) $CD264^-$ (white) and $CD264^+$ (black) MSCs. Representative phase-contrast micrographs of $CD264^-$ (C) and $CD264^+$ (D) cells. Scale bars: 100 µm. (E, F) Scatter properties of the sort groups. (G) Percentage of sorted cells staining positive for senescence-associated β-galactosidase activity. Data reported as mean±SEM for n=3. *$p<0.05$ and **$p<0.01$ vs. CD264-negative MSCs.

Heterogeneous MSCs were FACS (fluorescence activated cell sorting) sorted into CD264-negative and CD264-positive populations to evaluate the phenotype of each sort group (FIGS. 5A and B). In one embodiment, the sorted MSCs have 50% or more CD264- cells. In another embodiment, the sorted MSCs have 75% or more CD264- cells. In another embodiment, the sorted MSCs has 90% or more CD264- cells. FIG. 5B shows a purity of >99% CD264- MSCs after sorting. The phase-contrast micrographs reveal that $CD264^+$ MSCs were enlarged relative to $CD264^-$ MSCs (FIGS. 5C and D). This is consistent the increase in forward and side scatter from the $CD264^+$ group, which are indicative of larger and more granular cells, respectively ($p<0.05$, FIGS. 6E and F). Nearly 25% of $CD264^+$ MSCs stained positive for senescence-associated β-galactosidase vs. <3% for $CD264^-$ MSCs (p <0.01, FIGS. 5C, D and G). The morphology and elevated β-galactosidase activity of $CD264^+$ MSCs is consistent with an aging phenotype.

Figure 7:
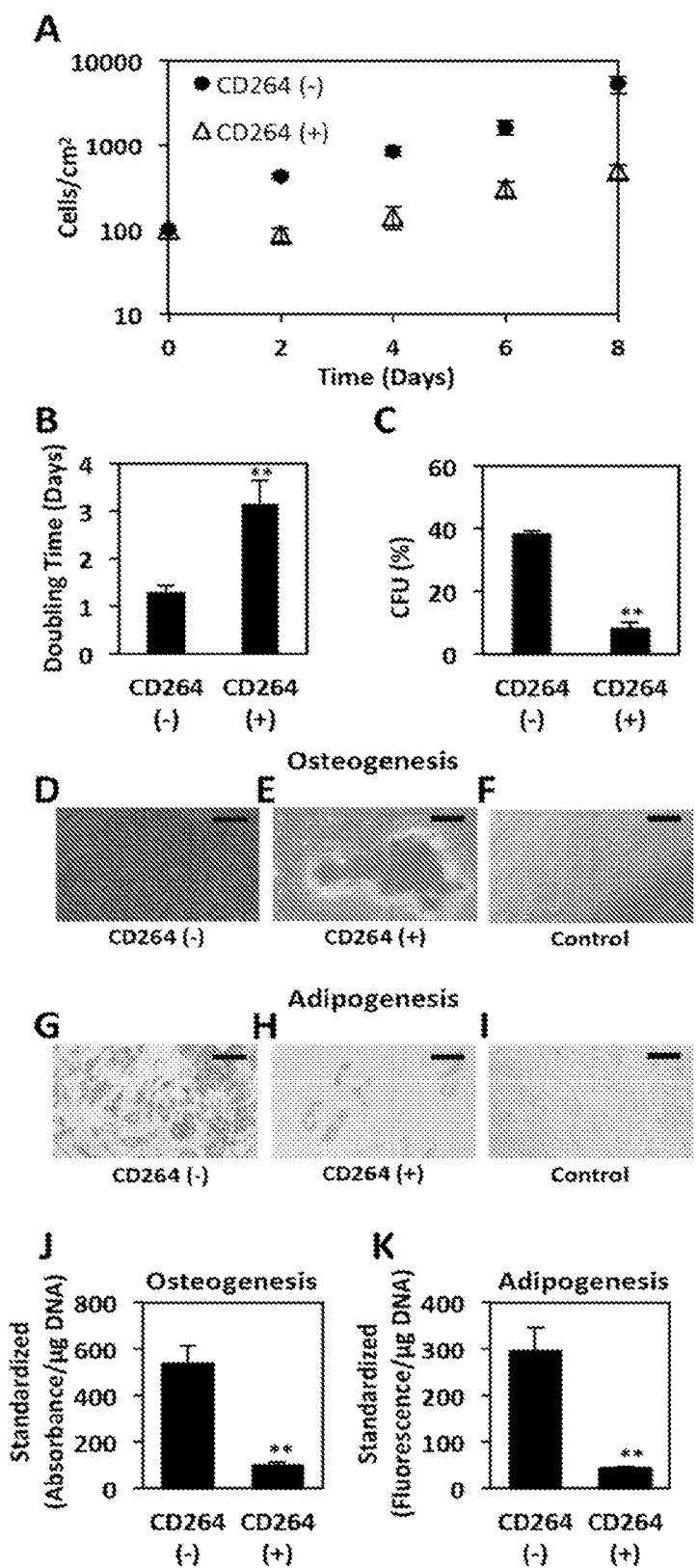
FIG. 7. Proliferation and differentiation potential of $CD264^-$ and $CD264^+$ MSCs. P3 MSCs were sorted based on CD264 expression as in FIG. 16. (A) Growth curve of $CD264^-$ (circles) and $CD264^+$ (triangles) MSCs. (B) Doubling time of sorted MSCs calculated from exponential growth phase of growth curve. (C) Efficiency of sorted cells to form colonies when plated at clonogenic levels. Differentiation potential of sorted MSCs was evaluated after 21 days in (D,E,J) osteogenic medium by staining with Alizarin Red S to detect mineralization and (G,H,K) adipogenic medium by staining lipids with AdipoRed™ from Lonza. Adipo Negative control cultures (F,I) in growth medium. Scale bars: 100 mm. Absorbance and fluorescence from extracted Alizarin Red S (J) and AdipoRed (K), respectively, are reported for each sort group per µg DNA and standardized relative to the negative control. Data reported as mean±SEM for n=3. *$p<0.05$ and **$p<0.01$ vs. CD264-negative MSCs.

Of the two sort groups, CD264+ MSCs had a significantly lower proliferation potential. When both sort groups were expanded ex vivo from an inoculum of 100 cells/$cm^2$, the cell density for the CD264- population was an order of magnitude higher after 8 days of amplification (FIG. 7A). This corresponds to a doubling time approaching once a day and every 3 days for CD264- and CD264+ MSCs, respectively ($p<0.01$, FIG. 7B).

FIG. 7C is a bar-graph showing the average colony forming efficiencies for P4 cells. CD264- cells displayed significantly greater colony forming potential than did CD264+ cells positive for death receptor ($p<0.01$). Error bars represent the average ±standard error of the mean. In fact, the CD264+ group formed clonogenic colonies ~4 times less efficiently ($p<0.01$, FIG. 7C). The limited proliferation potential of CD264+ MSCs (FIGS. 7A-C) coupled with their larger size and β-galactosidase staining (FIG. 5G) are classic features of cellular aging.

After the CD264- and CD264+ MSCs were cultivated in osteogenic medium for 3 weeks, Alizarin Red S staining detected extensive calcium deposition during matrix mineralization in the CD264- sort group; whereas, the CD264+ group consisted primarily of unstained cells with interspersed nodules of stained cells (FIGS. 7D-F). Absorbance from extracted Alizarin Red S is reported on an intrinsic basis per μg DNA and standardized to the negative control culture maintained in growth medium (FIG. 7J). This measure of osteogenesis was 5-fold less for CD264+ MSCs than for the CD264- group ($p<0.01$, FIG. 7J).

Similar results were obtained for adipogenesis (FIGS. 7G-I and K). As in the case of proliferation potential, CD264 selects for MSCs with compromised differentiation potential.

EXAMPLE 3

Passaging Effects on CD264 Expression

Figure 8:
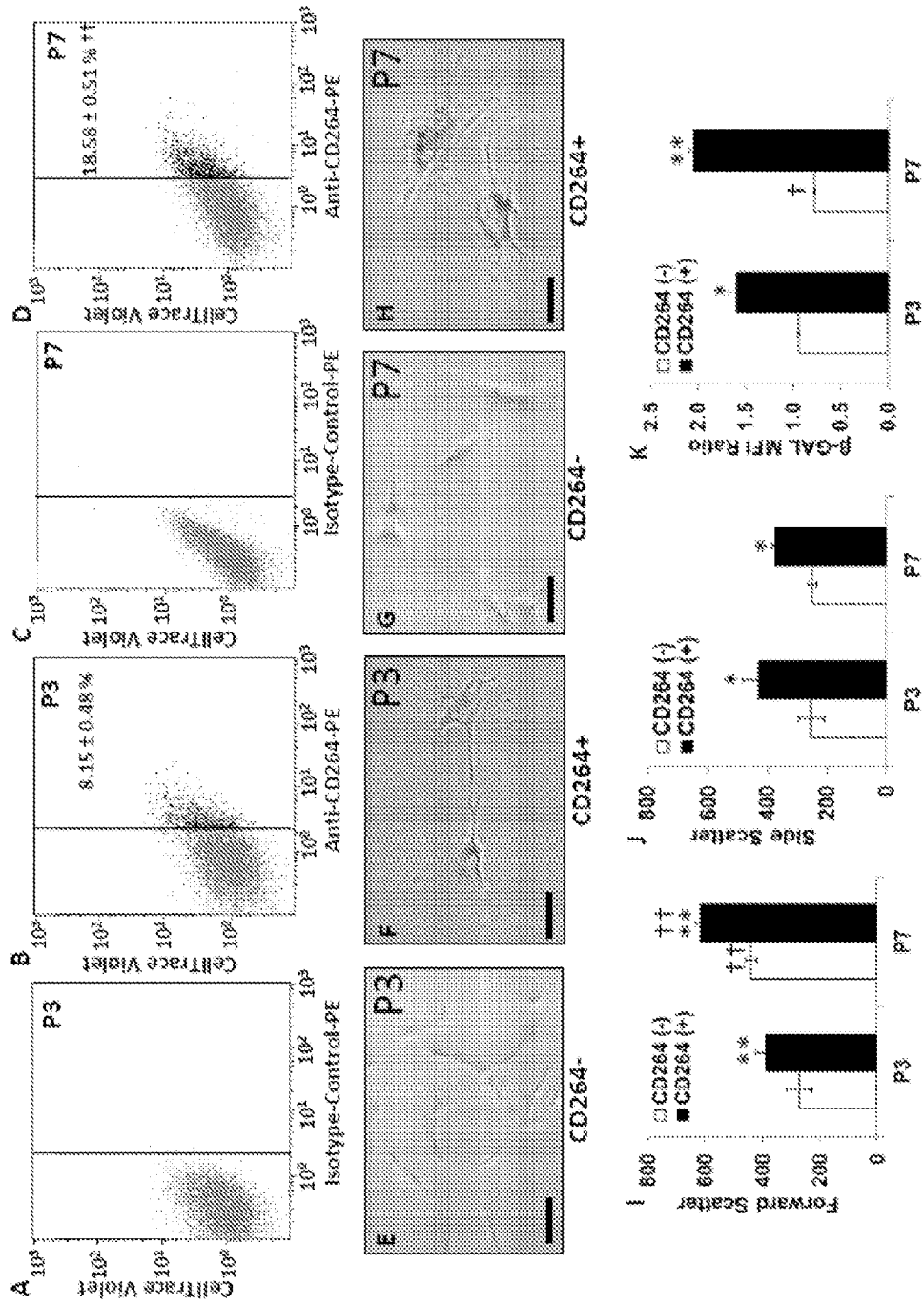
FIG. 8A-K shows phenotype comparison of CD264+ and CD264− MSCs during serial passage of parental MSC culture.

FIG. 8 shows phenotypic comparison of CD264+ and CD264- MSCs during serial passage of parental MSC culture, originally obtained from donor 7042R. Representative histograms from flow cytometric analysis of 10,000 cells of parental MSCs labeled with isotype (A, C) and anti-CD264-PE (B, D) at passage 3 (A, B) and passage 7 (C, D). Percentage of parental MSCs positive for CD264 surface expression is shown in the upper right of the histograms B and D. Representative micrographs of colorimetric staining of senescence-associated beta-galactosidase activity in MSCs at passage 3 (E, F) and passage 7 (G, H) sorted by FACS into CD264- (E, G) and CD264+ (F, H) groups. Scale bars: 50 μm (E-H). Flow cytometric analysis of scatter properties (I, J) and senescence-associated beta-galactosidase activity (K) for CD264+ and CD264- groups in parental MSCs at passage 3 and 7 (n=3). Mean fluorescent intensity ratio is presented relative to that of parental MSCs at the same passage. Data are reported as mean ±standard error of the mean. *$p<0.0.5$ and **$p<0.01$ vs. CD264- MSCs at same passage, †$p<0.05$ and ††$p<0.01$ vs. P3 MSCs of same CD264 group.

The content of CD264+ cells in MSC culture increases with serial passage: less that 10% at passage 3 to approximately 20% at passage 7 ($p<0.01$, FIGS. 8A-D). Even at early passage, the morphology of CD264+ MSCs is consistent with that of an aging cell: large size and granular cytoplasm. This is evident in the phase-contrast micrographs (FIGS. 8E-H) and in the scatter properties of the cells (FIGS. 8I & J). The forward scatter, which is indicative of cell size, is 30% -40% greater, on average, for CD264+ vs. CD264- MSC at passage 3 and 7 ($p<0.01$, FIG. 8I). The trend is similar for side scatter, which is a measure of cell granularity (FIG. 8J). Even at early passage, CD264+ MSCs stain positive for senescence-associated beta-galactosidase (FIG. 8F), and the staining intensity is more pronounced than in CD264− cells at each passage (FIGS. 8E-H). These qualitative results from microscopy were confirmed quantitatively by flow cytometric analysis of beta-galactosidase activity (FIG. 8K). Overall, these findings from serial passaged MSCs are consistent our analysis of proliferation and differentiation potential (FIG. 7) and depict CD264 as a marker of early MSC aging. This further supports the use of CD264 expression in early passages of MSCs as an indicator of aging.

EXAMPLE 4

Effects of Serial Passage on Expression of CD264 and Select Cell-Cycle Inhibitors Removal of CD264+ cells from the heterogeneous MSCs will provide an enriched, young population of MSCs. Other cell-cycle inhibitors are known to be upregulated in intermediate to late aging in MSCs, such as P53, p16 and p21. Correlating CD264 expression with these cell-cycle inhibitors with CD264 will provide even more accurate prediction of MSC aging. To determine the stage of aging in which CD264 is upregulated in MSCs, a time-course study of the expression of CD264 in serially passaged MSCs was conducted and compared the temporal profile for CD264 expression to that of select cell-cycle inhibitors, p53, p16 and p21. MSCs were strongly positive for p53 expression (data not shown): more than 80% of the cells were positive for this cell-cycle inhibitor throughout serial passage (data not shown). Expression of CD264 and p21 were upregulated concurrently first at P11 and continued to increase at P14 (data not shown). The percentage of CD264+ MSCs doubled between P3 and P14, and there was a similar increase for $p21^+$ cells (data not shown). Concurrent expression of CD264 and p21 indicates that CD264 is a cell-surface marker of an intermediate stage of replicative aging.

Figure 9:
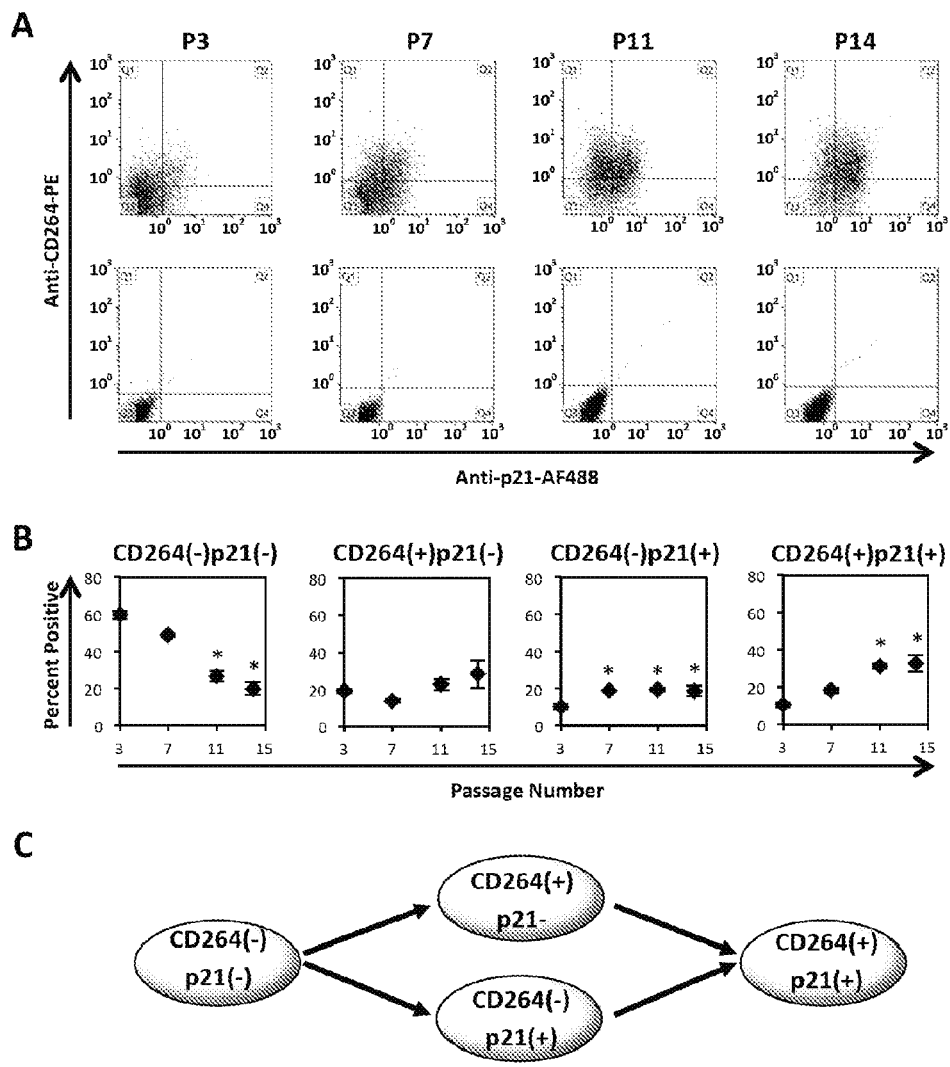
FIG. 9A-C. Co-expression of CD264 and p21 in serially passaged MSCs. MSCs were labeled with anti-CD264-PE, fixed, permeabilized, and co-labeled with anti-p21-AF488. (A) Representative bivariate histograms of co-labeled MSCs at select passages. (B) Corresponding percentages of MSCs that were CD264−p21−, CD264+p21−, CD264−p21+p21$^{30}$ and CD264−p21−.(C) Schematic of the conversion of C264+ p21+ MSCs to a CD264+p21+ phenotype. Data reported as mean±SEM for n =3. *p<0.05 vs. P3 MSCs.

MSCs have a primarily $CD264^-p21^-$ phenotype at early passage, and the fraction of $CD264^-p21^-$ cells decreased during serial passage as they progressed to one of two transitional states: $CD264^+p21^-$ or $CD264^-p21^+$ (FIG. 9A-B). While there was a pool of $CD264^-p21^-$ MSCs in culture, the fraction of $CD264^+p21^-$ and $CD264^-p21^+$ cells were fairly independent of passage number (FIG. 9B), and $CD264^+p21^-$ and $CD264^-p21^+$ cells converted to a $CD264^+p21^+$ phenotype, which accumulated at P11 and P14 (FIG. 9A-B). The schematic in FIG. 9C depicts the progression of MSCs from a $CD264^-p21^-$ phenotype through transitional states to a $CD264^+p21^+$ phenotype. The accumulation of $CD264^+p21^+$ MSCs during serial passage illustrates linkage between CD264 and p21. Therefore, in addition to CD264, co-expression of CD264 and p21 may be used as indicator of aging MSC populations.

Immense complexity is found in the heterogeneity of mesenchymal stem cell populations. CD264− cell cultures and conditioned media can be used to enhance therapies using MSCs to exclude cells with high expression of the cell death receptor. CD264 expression is present in early passage MSC populations, as early as passage 3 and accumulate over time. Avoiding the use of MSC's with CD264+ will enhance the effectiveness of stem cell therapies by providing more proliferation.

Heterogeneity is a major stumbling block to stem cell therapies. This invention presents sorting methods that will enhance the use of MSCs by providing a more robust population of MSCs possible from a donor.

Additionally, CD264 could be used to monitor cell aging during ex vivo expansion to generate sufficient amount of MSCs for therapeutic application. This marker may provide a means to remove aging cells during the production of MSC therapies.

CD264 is the only surface marker discovered for early MSC aging and thus can be used on a method for sorting heterogeneous MCS populations. There are numerous uses of this method in addition to sorting MSCs. CD264 can be used to identify biological agents and culture conditions that could slow the rate of MSC aging and potentially reverse the aging process.

This disclosure can be employed, for instance, to monitor MSC preparations in the clinic for consistent content of multipotent cells and to determine the variability in heterogeneity among different donors, with age and under different culture conditions. The content of CD264+ cells in an MSC therapy could potentially predict its efficacy for a variety of therapeutic applications. Additionally, CD264 could be used to remove aging cells during the production of MSC therapies.

The method of this disclosure can be used to identify other factors associated with MSC multipotency. Using this invention makes it possible to exploit differential growth kinetics to enrich multipotent cells in a heterogeneous MSC preparation during ex vivo amplification for clinical use by using the marker CD264. The ease of identification of MSCs with multipotency and efficient colony formation, and further culturing of the isolated MSCs with negative expression of CD264 can provide a source of MSCs for improved therapy and research.

Each of the following references is incorporated herein in its entirety for all purposes:

Wagner et al., How to Track Cellular Aging of Mesenchymal Stromal Cells? Aging, April 2010, Vol. 2, No. 4, 224-230.

Secchiero et al, Tumor Necrosis Factor-Related Apoptosis-Inducing Ligand Promotes Migration of Human Bone Marrow Multipotent Stromal Cells. Stem Cells 2008; 2955-2964.

Ren et al., SENESCENCE OF CULTURED BONE MARROW STROMAL CELLS. Biology of Blood and Marrow Transplantation, Feb. 2011; 17(2).

Degli-Esposti et al., The Novel Receptor TRAIL-R4 Induces NF-κB and Protects against TRAIL-Mediated Apoptosis, yet Retains an Incomplete Death Domain. Immunity (1997), Vol. 7, 813-820

Collado et al., Senescence in premalignant tumours. Nature (2005), Vol. 436, p. 642 (Supplementary Information).

Zhu et al., Effects of estrogen on stress-induced premature senescence of vascular smooth muscle cells: A novel mechanism for the "time window theory" of menopausal hormone therapy. Atherosclerosis 215 (2011) 294-300.

Kim et al., Evaluation of premature senescence and senescence biomarkers in carcinoma cells and xenograft mice exposed to single or fractionated irradiation. Oncology Reports 31: 2229-2235, 2014.

Russell et al., Cell-surface expression of neuron-glial antigen 2 (NG2) and melanoma cell adhesion molecule (CD146) in heterogeneous cultures of marrow-derived mesenchymal stem cells. Tissue Eng Part A, 19: 2253-66 (2013).

Russell et al., Clonal analysis of proliferation potential of human bone marrow mesenchymal stem cells as a function of potency. Biotechnol Bioeng, 108:2716-26 (2011).

US20120276064, Methods and compositions for rejuvenation and expansion of stem cells, published on Nov. 1, 2012.

US20140065112, Compositions and methods for mesenchymal/stromal stem cell rejuvenation and tissue repair by enhanced co-expression of telomerase and myocardin, published on Mar. 6, 2014.

US20140322811, Medium composition for rejuvenating stem cells, published on Oct. 30, 2014.

What is claimed is:

1. A method of identifying multipotent mesenchymal stem cells of high proliferation potential in early passages, comprising the steps of:
   a) collecting mesenchymal stem cells, the collected mesenchymal stem cells having not undergone more than five passages;
   b) measuring the expression of CD264 in the collected mesenchymal stem cells;
   c) removing the mesenchymal stem cells with positive expression of CD264; and,
   d) identifying CD264- cells as the multipotent mesenchymal stem cells of high proliferation potential.

2. The method of claim 1, wherein the step c) is carried out through using fluorescence-activated cell sorting.

3. The method of claim 1, further comprising:
   b-1) measuring the expression of p21; and
   c-1) removing the collected mesenchymal stem cells with positive expression of p21.

4. A method of identifying multipotent mesenchymal stem cells in early passages capable of high proliferation comprising the steps of:
   a) collecting mesenchymal stem cells, the collected mesenchymal stem cells having not undergone more than five passages;
   b) introducing fluorescent antibodies against CD264 to the collected mesenchymal stem cells;
   c) sorting the mesenchymal stem cells based on positive and negative CD264 expression;
   d) collecting the mesenchymal stem cells that are not bound by the fluorescent antibodies; and,
   e) identifying CD264- cells as the multipotent mesenchymal stem cells capable of high proliferation.

5. A method of identifying multipotent mesenchymal stem cells of high trilineage potential in early passages comprising the steps of:
   a) collecting mesenchymal stem cells, the collected mesenchymal stem cells having not undergone more than five passages;
   b) introducing fluorescent antibodies against CD264 to the collected mesenchymal stem cells;
   c) sorting the mesenchymal stem cells based on positive and negative CD264 expression;
   d) collecting the mesenchymal stem cells that are not bound by the fluorescent antibodies; and,
   e) identifying CD264- cells as the multipotent mesenchymal stem cells of high trilineage potential.

6. The method of claim 5, wherein the step c) is carried out through using fluorescence-activated cell sorting.

* * * * *